United States Patent [19]
Hubscher

[11] Patent Number: 5,244,788
[45] Date of Patent: Sep. 14, 1993

[54] METHOD AND APPARATUS FOR PERFORMING DETERMINATIONS OF IMMUNE RECTANTS IN BIOLOGICAL FLUIDS

[76] Inventor: Thomas T. Hubscher, 18912 Glendower Rd., Gaithersburg, Md. 20879

[21] Appl. No.: 907,355
[22] Filed: Jul. 1, 1992
[51] Int. Cl.⁵ ............................................. C12Q 1/00
[52] U.S. Cl. ....................................... 435/7.92; 435/4; 435/7.9; 435/7.94; 422/56; 422/57; 422/58
[58] Field of Search .................. 422/56, 57, 58; 435/4, 435/7.9, 7.92, 7.94

[56] References Cited

U.S. PATENT DOCUMENTS

| | | |
|---|---|---|
| 3,720,760 | 3/1973 | Bennich et al. . |
| 3,826,619 | 7/1974 | Bratu, Jr. et al. . |
| 3,891,507 | 6/1975 | Breuer . |
| 4,135,884 | 1/1979 | Shen . |
| 4,155,711 | 5/1979 | Zelagin et al. . |
| 4,200,613 | 4/1980 | Alfrey et al. . |
| 4,207,289 | 6/1980 | Weiss . |
| 4,225,575 | 9/1980 | Piasio et al. . |
| 4,276,259 | 6/1981 | Eibl et al. . |
| 4,336,337 | 6/1982 | Wallis et al. . |
| 4,472,357 | 9/1984 | Levy et al. . |
| 4,510,119 | 4/1985 | Hevey . |
| 4,591,570 | 5/1986 | Chang . |
| 4,599,315 | 7/1986 | Terasaki et al. . |
| 4,643,974 | 2/1987 | Berretti et al. . |
| 4,675,299 | 6/1987 | Witty et al. . |
| 4,761,378 | 8/1988 | Godsey . |
| 4,891,321 | 1/1990 | Hubscher ............................. 422/99 |

FOREIGN PATENT DOCUMENTS 0154687 9/1985 European Pat. Off. .
8907763 8/1989 PCT Int'l Appl. .

Primary Examiner—Sam Rosen

[57] ABSTRACT

A method and apparatus for performing determinations of immune reactants (e.g., antigens, antibodies) in bodily fluids utilize multiple test units having respective elongated rods with transversely-expanded polymer tips at their distal ends. The tip surfaces contain microgrooves and are coated with respective immune reactants (e.g., allergens) of the type which react in a known manner with respective allergen-specific or allergen-binding antibodies in human serum. The supporting strip for the test units has through-holes which frictionally or adhesively engage the proximal ends of the test unit rods with a spacing that permits all of the supported test units to be simultaneously inserted into a reaction vessel permitting simultaneous determination of reactants and degrees thereof against multiple immune reactants of varying kinds (i.e., allergens, antigens, antibodies) in a common sample of body fluid (i.e., serum, plasma, whole blood, etc.). The shallow microgrooves on the test tip permit rapid penetration of dye and rinsing of the test units. After incubation in the sample fluid, the test units are washed and then incubate in an enzyme-antibody conjugate. Upon additional rinsing the test units are permitted to incubate in a chromogenic substrate specific to the enzyme. The intensity of the resulting color (typically blue) on the tip is a measure of the amount of specific antibodies in the tested fluid sample.

20 Claims, 2 Drawing Sheets

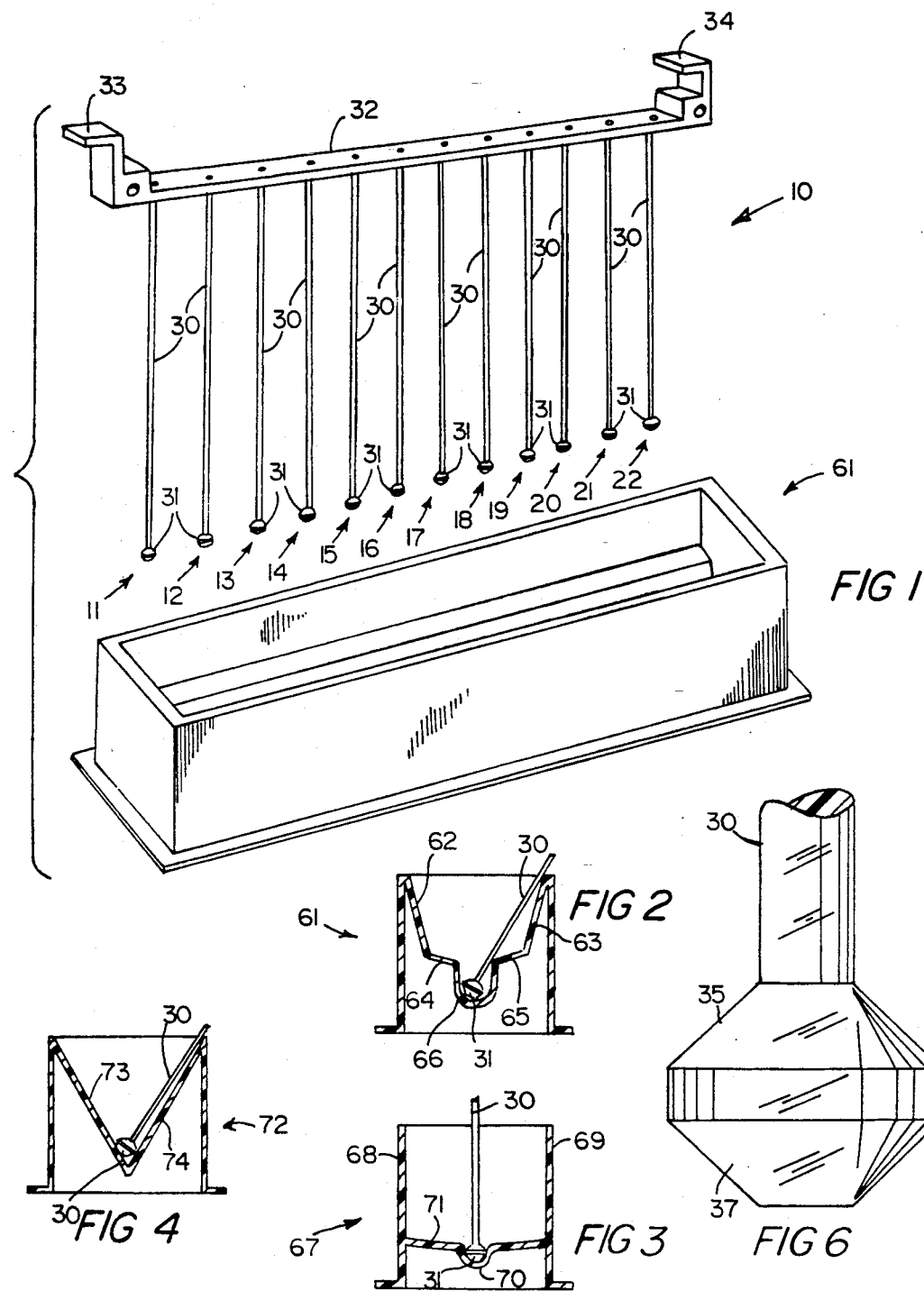

METHOD AND APPARATUS FOR PERFORMING DETERMINATIONS OF IMMUNE REACTANTS IN BIOLOGICAL FLUIDS

BACKGROUND OF THE INVENTION

1. Technical Field

The present invention relates to a method and apparatus for performing determination of immune reactants in biological fluids and, more particularly, for performing in vitro semi-quantitative determinations of allergen-specific (e.g., IgE, IgG, etc.) antibodies in human serum.

2. Discussion of the Prior Art

It is known that, in humans, immediate type allergic reactions (e.g., hay fever, extrinsic asthma, or atopic eczema) are mediated by reaginic antibodies belonging to the IgE class of immunoglobulins. Atopic individuals exposed to allergens such as pollens, dust or animal danders, produce specific IgE antibodies against these allergens. The present invention is concerned with determining the presence of circulating allergen-specific IgE antibodies in the blood plasma or serum of an affected individual.

A technique for accomplishing this result is known in the prior art as described in U.S. Pat. No. 3,720,760 (Bennich et al), the disclosure of which is expressly incorporated herein, in its entirety, by this reference. Specifically, Bennich et al disclose an in vitro method for analyzing a test sample (e.g., a body fluid such as blood serum or blood plasma) by contacting, in vitro, the test sample with a water insoluble polymer to which a test allergen has been bound. A reaction takes place between the test allergen on the polymer and the reagin-IgE directed against the allergen so that the reagin is bound to the test allergen on the insoluble polymer. The polymer, in sheet form, and with the test allergen and the reagin-IgE attached thereto, may then be contacted with antibodies against reagin-IgE that have been labeled with a radiation-emitting atom or group. The insoluble polymer sheet is separated from the fluid, whereupon the radiation emitted from the insoluble polymer with the substances attached thereto, or the radiation emitted from the separated fluid, is measured. If the reagin-IgE directed against the allergen is present in the sample, labeled reagin is bound to the insoluble phase which then emits radiation. The latter increases with increasing concentration of the reagin-IgE in the test sample. The radiation of the liquid phase decreases with increasing concentration of the reagin-IgE as more labeled reagin is bound to the insoluble phase. The measured radiation values obtained in this procedure for the test sample can be compared with values for control samples. If instead of radioimmunoassay (RIA) techniques, one were to use enzyme-immunoassay (EIA), color intensity, rather than radiation, becomes the measured parameter.

The use of polymer sheets as a vehicle to which the test allergen is bound, and to which the allergen-specific antibodies attach, becomes unwieldy in practice. To overcome the problem, the invention disclosed in my U.S. Pat. No. 4,891,321 employs multiple individual test units, each in the form of an elongated rod having an allergen-coated tip at its distal end. The proximal end of each rod is engaged in a support strip so that the test units are disposed in a position-identified linear array. Spacing between the test units matches the spacing between reaction containers in an assembly of such containers. The test units are inserted into respective reaction containers containing test serum. If there is an antibody specific to the allergen coated on any of the tips, that allergen-specific antibody becomes bound to the associated allergen in the corresponding reaction container. The tips are then washed, dried without rubbing, and inserted into a second set of reaction containers in which a suitable enzyme-labelled antibody conjugate has been poured. The test units are removed and rinsed once again and then placed into a third set of reaction containers containing chromogenic substrate that develops a specific color upon positive reaction. After incubation, the test units are removed and the remaining liquid in each reaction container is analyzed for color development and intensity by a suitable spectrophotometric analyzer.

This technique is reliable and greatly simplifies the portion of the Bennich et al method during which the polymer, to which a test allergen has been bound, is inserted into the test serum to permit circulating allergen specific IgE antibodies to attach to the bound allergen. However, it is desirable to reduce the time required to perform the method described in my prior patent and to eliminate the need for a costly spectrophotometric analyzer.

Another test apparatus known in the prior art for providing in vitro determinations of immune reactants in biological fluids is marketed by Quidel of San Diego, California as the Allergy Screen. This apparatus includes a fibrous test strip having successive pads or sections impregnated with specific allergens. The test strip is inserted into a test tube containing a serum or whole blood sample and left to incubate at room temperature for six hours or more. The manufacturer describes a quick test procedure involving only a thirty minute incubation period, but the sensitivity of this test is not acceptable for most procedures. After incubation the test strip is washed and then inserted into a second test tube containing conjugate solution for thirty minutes. Thereafter the test strip is washed again and then inserted into a third test tube containing a substrate for an additional thirty minutes. Upon removal from the third test tube the test strip is blotted on a paper towel until all pads are dry. The test strip is then mounted on a test result card with each test pad disposed adjacent a corresponding test strip. If the blue color intensity of any individual allergen test pad is greater than the intensity of a negative control pad, a positive result has been obtained. If the blue color intensity of a test pad is equal to or lighter than the intensity of the negative control pad, a negative result has been obtained.

The above-described Quidel Allergy Screen procedure takes at least seven hours for meaningful results and is not as sensitive as desired in that it tends to miss borderline allergic conditions. The reason for these problems appears to relate to the use of a test strip made of fibrous material such as cellulose paper. It requires a relatively long time for the reactants to penetrate the fibrous material and, once penetration occurs, to be washed out. In fact, once the reactants or dye penetrates the material, it is very difficult to rinse them out. The result is that both specific and non-specific dye gets trapped in the test strip.

OBJECTS AND SUMMARY OF THE INVENTION

It is therefore a primary object of the present invention to provide apparatus for performing in vitro determinations of immune reactants in biological fluids.

It is another object of the present invention to provide a novel immunoassay kit permitting simultaneous multiple tests for respective multiple allergen-specific antibodies in human serum/plasma.

It is a more general object of the present invention to provide an improved technique for diagnosing specific allergies in humans in a manner more efficient, faster and less costly than the methods described in U.S. Pat. Nos. 3,720,760 and 4,891,321.

It is another Object of the present invention to provide a test apparatus of the type described in which multiple individual test units can be coated with respective immune reactants (e.g., allergens) and supported in a manner to permit simultaneous insertion of all the test units into either a common container or into respective individual appropriate containers.

Yet another object of the present invention is to provide multiple test units for use in simultaneously testing blood serum, plasma or whole blood for the presence of respective allergen-specific antibodies, wherein visible changes in the individual test units signify a positive reaction between the allergen coated on the test unit and an antibody specific to that allergen in the test fluid.

In accordance with the present invention there is provided a method and apparatus for performing in vitro semi-quantitative determinations of allergen specific antibodies in human serum, plasma and/or whole blood. The method utilizes an enzyme-substrate color indicator that precipitates and localizes at the site of the immune reaction, namely on the surface of the polymer tip of a test unit, the tip being coated with the allergen (immune reactant). The precipitated color indicator and its intensity can be visualized and graded by the naked eye. According to the invention, multiple test units take the form disclosed in my aforesaid U.S. Pat. No. 4,891,321, namely an elongated rod having a tip coated with an allergen or anti-IgE at its distal end. The test units, which may have their rods colored or otherwise coded to identify the allergen (or anti-IgE) coating on the tip, are mounted to depend from a support strip so as to be simultaneously inserted into a reaction vessel. The latter may contain the test serum or plasma and an equal volume of an incubation medium such as buffered protein solution. The test unit tips are permitted to react with the liquid mixture in the vessel for thirty minutes at room temperature. If whole blood is employed as the test liquid, no incubation medium is required and the test unit tips are left to react with the whole blood for two hours. If the blood or serum contains an antibody specific to the allergen on any of the tips, that antibody becomes bound to the associated allergen. Importantly, the tips are hard plastic material, typically a hydrocarbon polymer such as polystyrene, etc., having microgrooves in its surface. Accordingly, dye quickly gets only into the shallow microgroove and washes out relatively easily. The tips are then washed three times for one minute each in three changes of distilled water and dried without rubbing. The vessel is washed with distilled water during the tip washing process. The tips are again inserted into the vessel into which a suitable specific antibody-enzyme conjugate (e.g., affinity purified goat anti-human IgE, conjugated with horseradish peroxidase) is added. The tips are then permitted to incubate in the conjugate for another thirty minutes at room temperature. During this incubation the peroxidase labeled anti-human IgE reacts with and specifically binds to the allergen specific IgE-antibodies bound to the allergen coated on the tips. The tips are once again washed three times for one minute each in three changes of distilled water and then reinserted into the vessel which is likewise washed. A specific substrate with an indicator in a precipitating formulation (e.g., hydrogen peroxide and 3,3',5,5' tetramethylbenzidine (TMB) is placed in the reaction vessel and the tips are permitted to incubate therein for another thirty minutes at room temperature. During this incubation a blue color, which intensifies with time, develops on the surface of those tips on which an allergen-antibody reaction took place. The test units are then gently removed from the holder and the intensity of the developed blue color is read by the naked eye as a measure of the allergen specific antibodies present in the tested serum or blood. The intensity of the blue color is typically graded on a scale of zero to five, where zero is the color of a negative control test unit tip and five is the color of a positive control test unit tip. A color and chart scoring scale is also used to visually quantify the results obtained on each allergen coated tip.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein like numerals in the various figures are utilized to designate like components, and wherein:

FIG. 1 is an exploded view in perspective showing one embodiment of the apparatus of the present invention;

FIG. 2 is a side view in section of a reaction vessel utilized in the apparatus of FIG. 1;

FIG. 3 is a side view in section of an alternative reaction vessel configuration;

FIG. 4 is a side view in elevation of still another reaction vessel configuration;

FIG. 6 is a side view in elevation of a test unit tip employed in the test units of FIG. 5.

DESCRIPTION OF THE PREFERRED EMBODIMENTS

Figure 5:
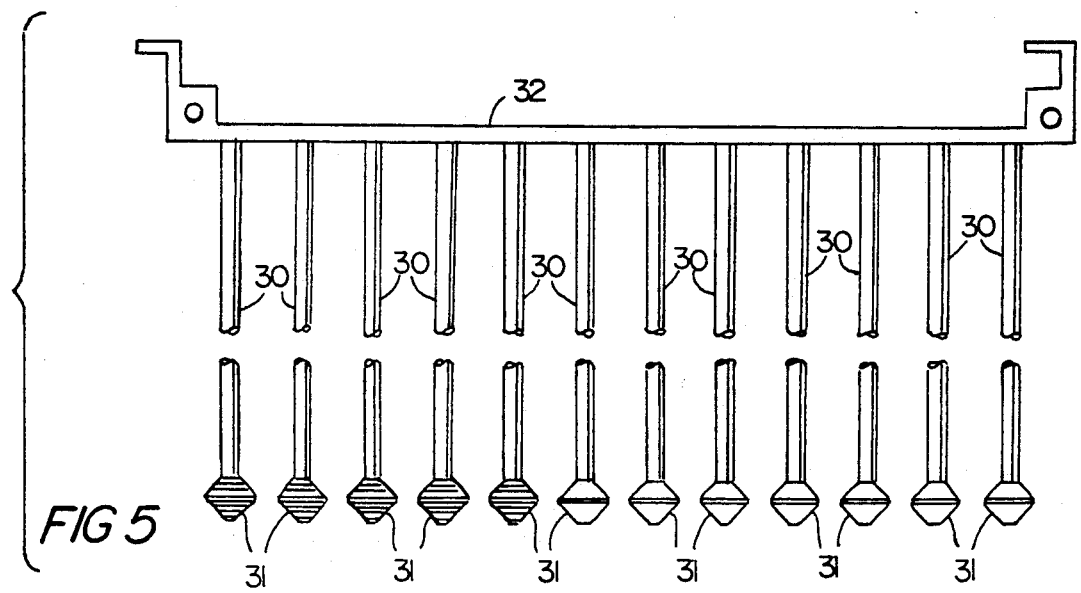
FIG. 5 is a front view in elevation of the support strip and test units employed in the apparatus of FIG. 1.

Referring specially to FIGS. 1-6 of the accompanying drawings, testing apparatus constructed in accordance with the principles of the present invention includes an array 10 of multiple test units 11 through 22, inclusive. Although twelve test units are provided in the preferred embodiment, it is to be understood that this number is not an essential feature of the invention and that any array of three or more test units may be employed. Each test unit is similar in configuration to the test units disclosed in my U.S. Pat. No. 4,891,321, the disclosure in which is expressly incorporated herein by this reference. Specifically, each test unit 11-22 includes an elongated cylindrical rod 30 with a transversely expanded tip 31 secured to its distal end. Rod 30 may be solid or hollow and has a section of reduced diameter at both its distal and proximal ends. The distal end is received in a suitable hole or aperture at the top of a respective tip 31 and is secured in place by adhesive, cement, or the like. The proximal end of the rod of each test unit 11-22 is removably engaged by a friction fit in a respective circular aperture or through-hole defined in an elongated holder strip 32. Alternatively, the rods may be secured in the strip holes by adhesive cement. The substantially identical apertures are disposed in a linear array along the length dimension of strip 32 with spaces of equal lengths between successive apertures. The apertures are positionally identified, as by molding the strip with position-identifying numbers adjacent each aperture. Alternatively, a printed gummed label may be attached to the strip to identify each aperture by position. The test units 11-22, therefore, with their rods 30 engaged in respective apertures, are supported in a linear array wherein the test units are suspended in side-by-side spaced relation with the spacing between successive test units preferably being the same. Holder strip 32 has handles/support brackets 33, 34 at its opposite ends to facilitate handling/support of the strip, and the supported test units, during test procedures.

Tip 31 is required to have a transversely or radially larger size than the diameter of the rod 30 in order to present a large surface area for adsorbing or otherwise bonding allergen material. As best illustrated in FIGS. 5 and 6, the tip 31 may take the form of three solid integrally-formed sections 35, 36 and 37. Section 35, the most proximal of the three sections, is frusto-conical with its smaller end apertured to receive the distal end of rod 30. The larger end of frusto-conical section 35 joins the axially shorter cylindrical section 36 which in turn joins the larger end of second frusto-conical section 37. The two frusto-conical sections 35 and 37 are of substantially equal axial length and identical shape but are inversely oriented axially so as to provide substantial symmetry on opposite sides of section 36. The surfaces of section 35, 36 and 37 may be smooth, as illustrated in FIG. 6, or multifaceted as described in my U.S. Pat. No. 4,891,321. The distal end of rod 30 is secured in the aperture defined in section 35 by means of suitable cement 38, adhesive, or the like.

Test unit rod 30 and tip 31 are made of a suitable water-insoluble polymeric material that is both rigid and capable of having the described allergen materials adsorbed on, or otherwise bonded to, the tip 31. The tip material should be transparent, translucent or white, and of a type which readily adsorbs the proteinaceous allergen materials and accepts the precipitated color indicator as described below. In this regard, the material of the tip inherently forms microgrooves at its surfaces to receive the allergen material and accept the color indicator. Examples of suitable polymeric materials for use in manufacturing test units 11-22 are hydrocarbon polymers such as polystyrene, polyethylene, polypropylene, polybutylene, butyl rubber and other synthetic rubbers, as well as polyesters, polyamides, vinyl and acrylic polymers such as polyvinyl chloride and polymethel methacrylate, cellulose and cellulose derivatives. In general, any organic polymeric material which adsorbs protein in relatively large amounts will be acceptable. The preferred substrate material for the test unit is impact grade polystyrene. The coating on tips 31 is achieved by dipping the tips into the antigen/allergen solution desired and thereafter following known procedures for suitable adsorption and/or chemical bonding. Importantly, all of the tips are initially of the same color (e.g., transparent, translucent or white or other light color).

As illustrated in FIG. 1, the suspended array 10 of test units 11-22 is used in conjunction with a common reaction vessel or container 61 formed as an integrally-molded plastic unit. Container 61 is open at its top and is sufficiently elongated to receive the tips 31 of all of the test units 11-22 simultaneously when strip 32 is lowered toward the container. Consequently, test units 11-22 may be simultaneously inserted into, or withdrawn from, reaction container 61 by hand or automated process. To this end, the open top of container 61 is very much wider than the transverse dimension of tips 31, thereby providing adequate clearance during insertion and withdrawal. In the preferred embodiment of container 61 the container is contoured to permit the test units to be supported by the container when tips 31 are disposed at the container bottom. Thus, as illustrated in FIG. 2, the interior sidewalls of container 61 may have first gradually converging sections 62, 63 extending downward from the top edges of the container to join more rapidly converging sections 64, 65. The bottom edges of sections 64, 65 are spaced on opposite sides of a centered longitudinal trough 66 of sufficient width to receive tips 31. When the tips are positioned in trough 66, rods 30 are supported by the lower end of wall section 65 and the top of the corresponding sidewall so that the entire supported array of test units 11-22 may be left unattended to incubate in a somewhat tilted orientation from vertical.

Alternatively, the reaction vessel may take the form of vessel 67 illustrated in FIG. 3 wherein the sidewalls 68, 69 do not necessarily converge and a centered trough 70 in bottom wall 71 is configured to frictionally engage the test unit tips 31. This frictional engagement permits the test unit array to be supported vertically (i.e., not tilted) in the reaction vessel. Still another alternative reaction vessel configuration 72 is shown in FIG. 4 and includes converging and intersecting sidewalls 73, 74. Tips 31 of the test units are placed at the bottom of the container so that rods 30 can be supported in tilted orientation along one or the other of sidewalls 73, 74.

Each of the test units 11-22 in the array 10 are coded so as to be visibly identifiable and distinguishable from other test units in the same array. The coding permits a technician to correlate the visible identifier for each test unit with the particular allergen adsorbed on the tip 31 of that test unit. This is accomplished by means of a chart or table correlating each visible identifier with a corresponding allergen. The visible identifier may be the color of the tip rod 30, a number of dots along the rod length, a number of circumferential stripes on the rod, or an alphanumeric code printed on a label secured to the rod 30 or holder 32. In the preferred embodiment described herein, the coded visible identifier is an alphanumeric label. Typical alphanumeric codes employed for the test units are represented in Table I which is an example of an allergen correlation chart supplied with the apparatus of the present invention. The chart includes a first column listing the alphanumeric codes, and a second column listing the respective allergens adsorbed on each test unit tip.

TABLE I

| Code | Allergen |
| --- | --- |
| Neg | Negative Control |
| IGE | Total IgE |
| POS | Positive Control |

TABLE I-continued

| Code | Allergen |
|---|---|
| T07 | Oak Tree |
| G08 | Kentucky Blue grass |
| W01 | Ragweed-short |
| E01 | Cat epithelium |
| E05 | Dog dander |
| M06 | Alternaria mold |
| M02 | Cladosporium mold |
| D01 | Dust mite (*D. farinae*) |

The general principles of the test procedures in which the above-described apparatus is employed may be understood from the following brief description. A specific allergen, coated to a solid phase support on each tip 31, reacts with allergen-specific IgE antibodies in the patient's serum or blood. After washing away non-specific reactants, enzyme-labeled (peroxidase) anti-human IgE" reacts with the allergen-bound human IgE. After further washing, the bound complex "allergen"—"IgE"—"peroxidase anti-human IgE is caused to react with a chromogenic substrate specific for the peroxidase enzyme. This results in the development of a blue color on the surface of the reacting tip. The intensity of the developed blue color is directly proportional to the amount of circulating allergen-specific antibodies in the serum tested. Semi-quantation of these antibodies can be achieved visually by comparing the intensity of the developed color to scoring color chart accompanying the test system/apparatus. Alternatively, scoring can be based on a comparison of the blue colored tips 31 to the negative control (zero) and positive control (five).

A typical test procedure using the apparatus of the present invention is set forth in the following steps:

1. For each patient serum to be tested, one reaction container 61, 67 or 72 is set in place.
2. 1.5 ml of test serum is then placed in the reaction container. It is remembered that the reaction container is dedicated to a particular patient and that only the test serum for that patient is employed in the disposable container.
3. 1.5 ml of incubation medium is then placed in the reaction container 61. A typical incubation medium would be a buffered protein solution containing preservatives.
4. The array 10 of test units, supported by holder strip 32, is then removed from the plastic bags in which it is supplied. Care is taken not to touch the tips 31 which are coated with specific allergen material. It is also important that the test units not be removed from the holder strip 32 until the end of the procedure.
5. Test units 11–22 are then inserted simultaneously into the reaction container. The test units may be moved up and down slightly to ensure proper mixing.
6. The inserted test units are permitted to remain in place to achieve incubation for approximately thirty minutes at room temperature.
7. The test units, still supported by the holder strip 32, are then rinsed for at least one minute by filling the dish with distilled water. Three such rinsing cycles should be performed, with all of the water drained or otherwise changed between cycles. Reaction container 61 is similarly rinsed.
8. The test units are then placed on an adsorbent paper towel with care being taken not to rub the tips 31.
9. 3.0 ml of antibody conjugate is placed by a pipette into the reaction container 61. The antibody conjugate may be an affinity purified anti-human IgE (goat) conjugated to horseradish peroxidase in a buffer with stabilizers and preservatives.
10. Test units 11–22 are gently tapped on the absorbent towel and then placed into the reaction container 61 containing the antibody conjugate.
11. The inserted test units are permitted to incubate for approximately thirty minutes at room temperature.
12. The test units are removed from the reaction containers and washed and dried, along with container 61, by repeating steps 7 and 8 described above.
13. Reaction container 61 receives 3.0 ml of chromogenic substrate by means of a pipette. A typical substrate is hydrogen peroxide and 3,3',5,5' tetramethylbenzidine.
14. Test units 11–22 are gently tapped on the paper towels and placed into the reaction container 61 containing the chromogenic substrate.
15. Incubation is permitted to occur for thirty minutes at room temperature.
16. The test units are gently removed from the reaction container.
17. The test units are removed from the container and the intensity of the blue color that develops on the surface of the tips is visually graduated on a scale of zero to five by either using the color scoring chart provided with the apparatus, or comparing the colors of each individual tip with that of the Negative Control—score zero, and that of the Positive Control—score five. Depending on the nature of the assay, the Positive Control can also be assigned a score of only three, but reactions are graded all the way to a score of five.

It is important to note that the color developed on the test tips can be preserved for at least many months by rinsing the tips in distilled water and then permitting them to be dried in air.

Although the preferred embodiment of the present invention utilizes a single or common reaction container 61, 67, 72 or the like, it will be appreciated that the test units may be employed with individual containers, such as test tubes, or the containers described in my U.S. Pat. No. 4,891,321. If individual containers are employed, the present invention differs from my prior invention by the fact that the measured reaction takes placed on the test unit tips, not in the liquid remaining in the reaction containers. Accordingly, whatever type container is employed, the present invention eliminates the need for a spectrophotomic analysis of the liquid and thereby permits the tests to be achieved more rapidly and economically.

For a typical embodiment, the components of the invention described above have the dimensions indicated in my aforesaid prior patent. Container 61 is typically 4.375 inches long between its interior end walls and 1.1875 inches wide between the tops of its interior sidewalls. Recess 66 is typically 0.3125 inches deep and 0.3125 inches wide. It is to be understood that the dimensions set forth above are by way of example and not limiting on the scope of the present invention.

The invention, as described in terms of the preferred embodiment, utilizes an antibody labelled with peroxidase enzyme and a chromogenic substrate specific thereto. It is to be understood, however, that this is by way of example only and not a limitation on the scope of the invention. Another example would be alkaline-phosphatase enzyme with its corresponding paranitrophenyl substrate.

The invention as thus far described is specific to testing for allergen-specific antibodies, as well as IgE immunoglobulin, in human bodily fluids. It is to be understood that the apparatus described herein, and its method of use, apply to testing other antigens, in animal and human fluids, such as bacterial, viral, or auto-antigens (i.e., lupus, DNA, etc.).

An important aspect of the present invention is that the test tips 31 have only a surface with microgrooves into which the dye penetrates as compared to the deep porous penetration occurring in cellulose paper test strips. As a result, penetration is rapid and rinsing is relatively easy.

From the foregoing description it will be appreciated that the invention makes available a novel apparatus for performing determinations of allergen-specific antibodies in human serum, plasma, whole blood, etc., as well as a step-by-step procedure for making such determinations.

Having described preferred embodiments of a new and improved method and apparatus for performing determinations of allergen-specific IgE antibodies in human serum, while blood, plasma, etc., in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method for performing in-vitro determinations of immune reactants in biological fluids of humans or animals, said method comprising the steps:
   (a) simultaneously incubating a plurality of test units in a sample of biological fluid at room temperature, each test unit including an elongated rod having proximal and distal ends and a tip secured at said distal end, wherein said tips have different respective coatings of immune reactant material, allergens or IgE on their surfaces, each coating being of the type that reacts in a known manner with a respective corresponding immune reactive counterpart in the biological fluid sample, said incubating being sufficient to permit any antibodies in the test fluid that are specific to an allergen coating on one of said tips to become bound to that allergen coating;
   (b) rinsing said tips after incubation pursuant to step (a);
   (c) incubating said tips at room temperature, after rinsing pursuant to step (b), in a suitable specific antibody-enzyme conjugate to permit the conjugate to react with and specifically bind to antibodies that have become bound to allergen coatings in step (a);
   (d) rinsing said tips after incubation pursuant to step (c); and
   (e) incubating said tips at room temperature in a chromogenic substrate specific to the enzyme in said conjugate to permit a predetermined color to develop on the tip surfaces to which antibodies are bound pursuant to step (a), wherein the intensity of said predetermined color on each tip is a measure of the amount of antibodies in the test fluid sample that are specific to the allergen coating on that tip.

2. The method of claim 1 wherein said sample is serum and step (a) includes incubating said test units in said sample for a period of approximately thirty minutes.

3. The method of claim 2 wherein step (b) includes rinsing said tips in distilled water for at least three minutes.

4. The method of claim 1 wherein step (c) includes incubating said test units in said conjugate for a period of approximately thirty minutes at room temperature.

5. The method of claim 4 wherein step (d includes rinsing said tips in distilled water for at least three minutes.

6. The method of claim 1 wherein step (e) includes incubating said tips in said substrate at room temperature for at least thirty minutes.

7. The method of claim 1 wherein steps (a), (c) and (e) each include incubating said test units in said sample, in said conjugate and in said substrate, respectively, for approximately thirty minutes each.

8. The method of claim 1 wherein said sample is whole blood and step (a) includes incubating said test units in said sample for approximately two hours.

9. The method of claim 1 wherein said conjugate employed in step (c) is affinity purified goat anti-human IgE, conjugated with horseradish peroxidase.

10. The method of claim 1 wherein said substrate employed in step (e) is hydrogen peroxide and 3,3',5,5' tetramethylbenzidine.

11. The method of claim 1 wherein steps (b) and (d) each include rinsing said tips for approximately one minute in distilled water, changing the distilled water and rinsing the tips for approximately one more minute, and then changing the distilled water again and rinsing the tips for approximately one more minute.

12. A method for performing in-vitro determinations of immune reactants in biological fluids of humans or animals using a plurality of test units, each test unit including an elongated rod having proximal and distal ends and a tip secured at said distal end, said method comprising the steps of:
   (a) coating said tips with different reactive coatings of immune reactants, allergens or IgE, each coating being of the type that reacts in a known manner with a respective corresponding immune reactive counterpart in biological fluid;
   (b) simultaneously incubating the plurality of test units in a common sample of biological fluid to permit antibodies specific to a coating on said tips to become bound to that coating;
   (c) rinsing said tips after incubation pursuant to step (b);
   (d) incubating said tips after rinsing pursuant to step (c) in a suitable specific antibody-enzyme conjugate to permit the conjugate to react with and specifically bind to antibodies that have become bound to allergen coatings in step (b);
   (e) rinsing said tips after incubation pursuant to step (d); and
   (f) incubating said tips in a chromogenic substrate specific to said enzyme to permit a predetermined color to develop on the surface tips to which antibodies are bound pursuant to step (a), wherein the intensity of said predetermined color on each tip is a measure of the amount of antibodies in the test fluid that are specific to the coating on that tip.

13. The method of claim 12 wherein said predetermined color is blue.

14. The method of claim 12 further comprising the step of reading with the naked eye the color intensity on said tips and grading that color intensity by comparison to negative and positive control color intensities.

15. The method of claim 12 wherein steps (b), (d), and (f) each include incubating said test units in said sample, said conjugate and said substrate, respectively, for approximately thirty minutes each.

16. The method of claim 12 wherein said sample is whole blood and step (b) includes incubating said test units in said sample for approximately two hours.

17. The method of claim 12 wherein said conjugate employed in step (d) is affinity purified goat anti-human IgE, conjugated with horseradish peroxidase.

18. The method of claim 12 wherein said substrate employed in step (f) is hydrogen peroxide and 3,3',5,5' tetramethylbenzidine.

19. The method of claim 12 wherein steps (c) and (e) each include rinsing said tips for approximately one minute in distilled water, changing the distilled water and rinsing the tips for approximately one more minute, and then changing the distilled water again and rinsing the tips for approximately one more minute.

20. The method of claim 12 further comprising the steps of:
  (g) rinsing said tips after incubation pursuant to step (f); and
  (h) permitting the tips rinsed in step (g) to dry in air to preserve color developed on said tips.

* * * * *